US011355242B2

(12) United States Patent
Sailer et al.

(10) Patent No.: US 11,355,242 B2
(45) Date of Patent: Jun. 7, 2022

(54) MEDICAL TREATMENT MANAGEMENT

(71) Applicant: International Business Machines Corporation, Armonk, NY (US)

(72) Inventors: Anca Sailer, Scarsdale, NY (US); Kevin Paul Julier, Ridgefield, CT (US); Ajay Mohindra, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 423 days.

(21) Appl. No.: 16/537,699

(22) Filed: Aug. 12, 2019

(65) Prior Publication Data
US 2021/0050107 A1    Feb. 18, 2021

(51) Int. Cl.
*G16H 50/20*   (2018.01)
*G16H 50/70*   (2018.01)
*G16H 30/20*   (2018.01)
*G06F 16/953*  (2019.01)

(52) U.S. Cl.
CPC ......... *G16H 50/20* (2018.01); *G06F 16/953* (2019.01); *G16H 30/20* (2018.01); *G16H 50/70* (2018.01)

(58) Field of Classification Search
CPC ........ G16H 50/20; G16H 50/70; G16H 30/20; G06F 16/953
USPC ..................................................... 705/2, 3
See application file for complete search history.

(56) References Cited

U.S. PATENT DOCUMENTS 9,721,191 B2   8/2017  Song et al.
9,958,866 B2   5/2018  Chefalas et al.
10,126,746 B2  11/2018 O'Brien et al.
2009/0299766 A1* 12/2009 Friedlander ............ G06Q 10/00
                                                       705/3
2010/0017225 A1*  1/2010 Oakley .................. G16H 15/00
                                                       705/2

(Continued)

FOREIGN PATENT DOCUMENTS

CN          104116496 A     10/2014

OTHER PUBLICATIONS

Hossain et al, "Real-time Surgical Tools Recognition in Total Knee Arthroplasty Using Deep Neural Networks", 2018 Joint 7th ICIEV and 2018 2nd icIVPR, Jun. 25-29, 2018, pp. 470-474 (Year: 2018).*

(Continued)

*Primary Examiner* — John P Go
*Assistant Examiner* — Christopher B Wehrly
(74) *Attorney, Agent, or Firm* — James L. Olsen

(57) ABSTRACT

Aspects of the present disclosure relate to medical treatment management. Medical data associated with a user is received. A medical condition of the user is identified based on the medical data. Object data of a plurality of objects in a vicinity of the user is received. The object data is analyzed to determine an identity and characteristics of each object of the plurality of objects. The plurality of objects are compared to medical tools in a medical database using the characteristics within the object data. A subset of objects matching to respective medical tools are then identified. A medical procedure utilizing at least one object of the subset of objects to address the medical condition is identified. A recommendation is then transmitted that the medical procedure should be used to address the medical condition using the at least one object.

10 Claims, 7 Drawing Sheets

(56) References Cited

U.S. PATENT DOCUMENTS

| | | | |
|---|---|---|---|
| 2014/0347392 | A1 | 11/2014 | Odessky et al. |
| 2017/0169561 | A1 | 6/2017 | Mullins |
| 2017/0323062 | A1 | 11/2017 | Djajadiningrat et al. |
| 2018/0042681 | A1* | 2/2018 | Jagga ................ A61B 6/02 |
| 2019/0087544 | A1* | 3/2019 | Peterson ............. G16H 10/60 |
| 2019/0392953 | A1* | 12/2019 | Steuer ............... G06T 7/0012 |

OTHER PUBLICATIONS

Nicolas Maillot, "Ontology Based Object Learning and Recognition," Interface homme-machine [cs.HC], Université Nice Sophia Antipolis, 2005 tel-00327542 (Year: 2005).*

Hossain et al., "Real-time Surgical Tools Recognition in Total Knee Arthroplasty Using Deep Neural Networks", 2018 Joint 7th International Conference on Informatics, Electronics & Vision (ICIEV) and 2018 2nd International Conference on Imaging, Vision & Pattern Recognition (icIVPR), Jun. 25-29, 2018, pp. 470-474.

Redmon et al., "You Only Look Once: Unified, Real-Time Object Detection", May 9, 2016, 10 pages.

Letouzey et al., "Instruments Localisation and Identication for Laparoscopic Surgeries", 2016, 8 pages.

Choi et al., "Surgical-tools Detection based on Convolutional Neural Network in Laparoscopic Robot-assisted Surgery", 2017 39th Annual International Conference of the IEEE Engineering in Medicine and Biology Society (EMBC), Jul. 11-15, 2017, pp. 1756-1759.

Mell et al., "The NIST Definition of Cloud Computing", Recommendations of the National Institute of Standards and Technology, Sep. 2011, 7 pages.

* cited by examiner

MEDICAL TREATMENT MANAGEMENT

BACKGROUND

The present disclosure relates generally to the field of medical treatment, and more specifically to medical treatment recommendations.

SUMMARY

Embodiments of the present disclosure relate to a method, computer program product, and system for medical treatment management. Medical data associated with a user can be received. A medical condition of the user can be identified based on the medical data. Object data of a plurality of objects in a vicinity of the user can be received. The object data can be analyzed to determine an identity and characteristics of each object of the plurality of objects. The plurality of objects can be compared to medical tools in a medical database using the characteristics within the object data. A subset of objects matching to respective medical tools can then be identified. A medical procedure utilizing at least one object of the subset of objects to address the medical condition can be identified. A recommendation can then be transmitted that the medical procedure should be used to address the medical condition using the at least one object.

The above summary is not intended to describe each illustrated embodiment or every implementation of the present disclosure.

BRIEF DESCRIPTION OF THE DRAWINGS

The drawings included in the present disclosure are incorporated into, and form part of, the specification. They illustrate embodiments of the present disclosure and, along with the description, serve to explain the principles of the disclosure. The drawings are only illustrative of typical embodiments and do not limit the disclosure.

Figure 1:
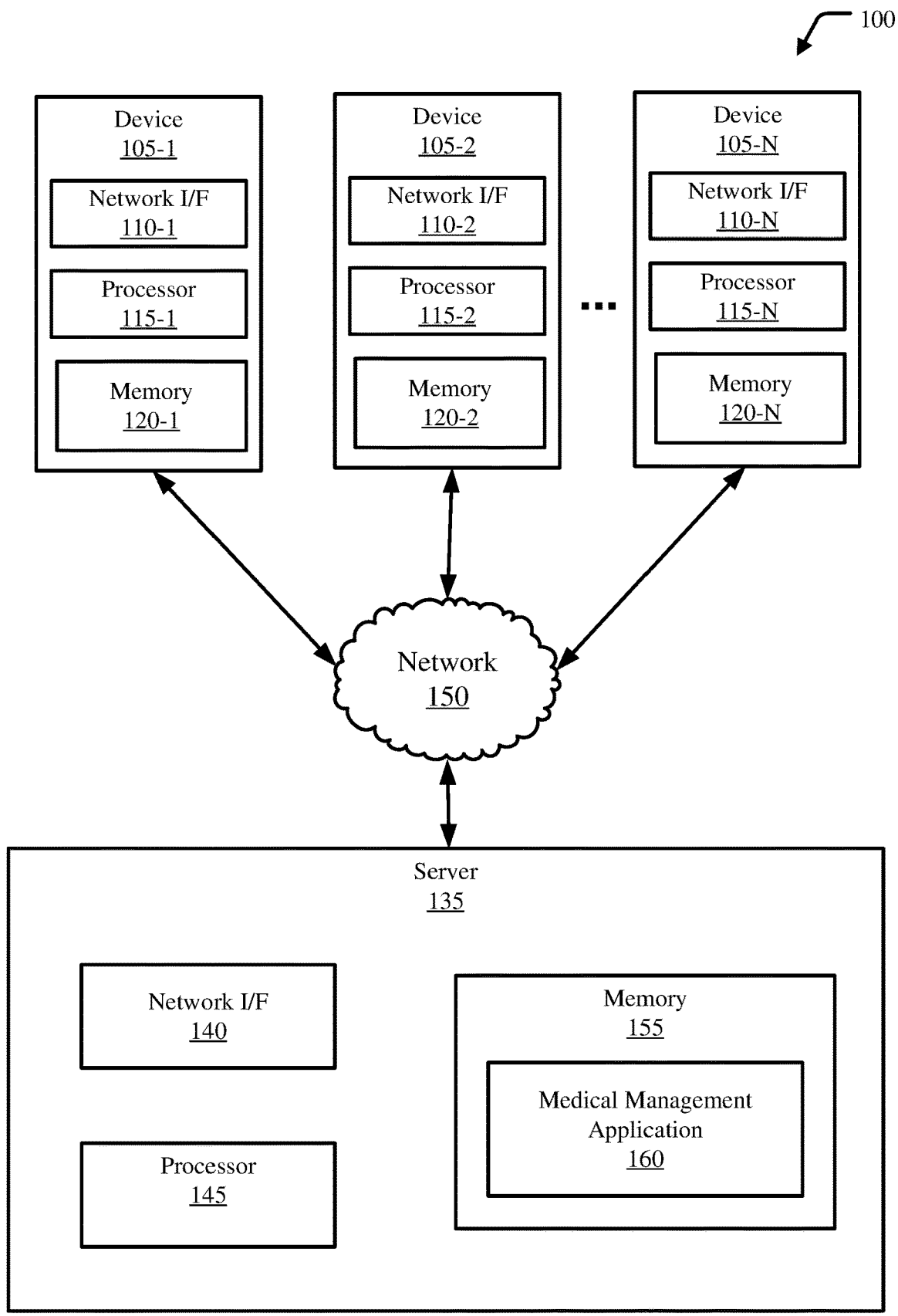
FIG. 1 is a block diagram illustrating an example computing environment in which illustrative embodiments of the present disclosure can be implemented.

While the embodiments described herein are amenable to various modifications and alternative forms, specifics thereof have been shown by way of example in the drawings and will be described in detail. It should be understood, however, that the particular embodiments described are not to be taken in a limiting sense. On the contrary, the intention is to cover all modifications, equivalents, and alternatives falling within the spirit and scope of the disclosure.

DETAILED DESCRIPTION

Aspects of the present disclosure relate generally to the field of medical treatment, and more particularly to medical treatment recommendations. While the present disclosure is not necessarily limited to such applications, various aspects of the disclosure can be appreciated through a discussion of various examples using this context.

Remotely located individuals have limited access to quality medical support. For example, personnel in outdoor/wilderness environments may not have access to proper medical equipment (e.g., scalpels, stitches, crutches, bandages, etc.), medicine (e.g., analgesics, antibiotics, etc.) or medical experts (e.g., doctors, nurses, medics, etc.) This can lead to improper diagnosis and treatment of medical conditions, which may worsen the outcome of the medical condition.

Though proper medical equipment (e.g., a first-aid kit) may be available to remotely located individuals, this equipment may not suffice in all situations. For example, the ability for on-hand medical equipment to address a medical condition can vary depending on the specific condition (e.g., broken leg, puncture wound, etc.), the severity of the condition, the environment (e.g., a forest, the desert, a mountain, etc.), and preexisting conditions (e.g., diabetes, anemia, etc.). As medical conditions have unique needs, it is unlikely that a remotely located individual, even in possession of limited medical equipment, has the proper tools to treat their condition. As such, aspects of the present disclosure recognize that limited medical equipment may be available to remotely located individuals, and as a result, treating medical conditions can be complicated.

Aspects of the present disclosure address the aforementioned complications via a medical management system. The medical management system can be configured to receive medical data of an individual. The medical data can be analyzed to determine a medical condition (e.g., a cut, a fracture, a rash, etc.) of the individual. The medical management system can then be configured to receive object data and identify objects that match to respective medical tools. A medical procedure utilizing the objects that match to respective medical tools can then be determined. The medical management system can then transmit the medical procedure including a recommendation that the objects that match to the respective medical tools can be used to implement the medical procedure.

In embodiments, if no suitable objects are available to complete a recommended medical procedure, the medical management system can be configured to prompt a user to provide additional data. This can be completed such that additional object data can be captured to potentially identify needed equipment to carry out a medical procedure.

The medical management system provides several advantages for individuals in need of medical treatment. First, aspects of the present disclosure enable the identification of a medical condition associated with an individual based on medical data provided by that individual. This allows for personalized diagnosis based on, for example, images provided by an injured individual. Aspects further enable identification of medical procedures which can be used to address the identified condition. These can be provided to the individual such that they have the knowledge required to provide support to their condition. Further still, aspects identify and recommend objects to be used as medical tools to carry out an identified medical procedure. This allows individuals to utilize available tools to carry out the medical procedure. For example, remotely located individuals may not have access to medical tools indicated in the medical procedure used to address their condition, and, as such, the system can be configured to provide recommendations of objects in their vicinity which can be used in substitute of medical tools which they do not have access to. Ultimately, the medical management system can improve the treatment of medical conditions and prevent worsening of medical conditions.

As discussed herein, "medical treatment" can refer to care given to an individual for an illness or injury. Medical treatment may not ensure actual recovery, but rather may indicate an attempt to address (e.g., care for, cure, aid, support, etc.) a medical condition.

Turning now to the figures, FIG. 1 is a block diagram illustrating an example computing environment 100 in which illustrative embodiments of the present disclosure can be implemented. Computing environment 100 includes a plurality of devices 105-1, 105-2 . . . 105-N (collectively devices 105), at least one server 135, and a network 150.

Consistent with various embodiments, the server 135 and the devices 105 are computer systems. The devices 105 and the server 135 include one or more processors 115-1, 115-2 . . . 115-N (collectively processors 115) and 145 and one or more memories 120-1, 120-2 . . . 120-N (collectively memories 120) and 155, respectively. The devices 105 and the server 135 can be configured to communicate with each other through internal or external network interfaces 110-1, 110-2 . . . 110-N (collectively network interfaces 110) and 140. The network interfaces 110 and 140 are, in some embodiments, modems or network interface cards. The devices 105 and/or the server 135 can be equipped with a display or monitor. Additionally, the devices 105 and/or the server 135 can include optional input devices (e.g., a keyboard, mouse, scanner, video camera, or other input device), and/or any commercially available or custom software (e.g., browser software, communications software, server software, natural language processing software, search engine and/or web crawling software, image processing software, etc.). The devices 105 and/or the server 135 can be servers, desktops, laptops, or hand-held devices.

The devices 105 and the server 135 can be distant from each other and communicate over a network 150. In some embodiments, the server 135 can be a central hub from which devices 105 can establish a communication connection, such as in a client-server networking model. Alternatively, the server 135 and devices 105 can be configured in any other suitable networking relationship (e.g., in a peer-to-peer (P2P) configuration or using any other network topology).

In some embodiments, the network 150 can be implemented using any number of any suitable communications media. For example, the network 150 can be a wide area network (WAN), a local area network (LAN), an internet, or an intranet. In certain embodiments, the devices 105 and the server 135 can be local to each other, and communicate via any appropriate local communication medium. For example, the devices 105 and the server 135 can communicate using a local area network (LAN), one or more hardwire connections, a wireless link or router, or an intranet. In some embodiments, the devices 105 and the server 135 can be communicatively coupled using a combination of one or more networks and/or one or more local connections. For example, the first device 105-1 can be hardwired to the server 135 (e.g., connected with an Ethernet cable) while the second device 105-2 can communicate with the server 135 using the network 150 (e.g., over the Internet).

In some embodiments, the network 150 is implemented within a cloud computing environment, or using one or more cloud computing services. Consistent with various embodiments, a cloud computing environment can include a network-based, distributed data processing system that provides one or more cloud computing services. Further, a cloud computing environment can include many computers (e.g., hundreds or thousands of computers or more) disposed within one or more data centers and configured to share resources over the network 150.

The server 135 includes a medical management application 160. The medical management application 160 can be configured to provide support to an individual experiencing a medical condition. To do so, the medical management application 160 can first be configured to analyze (e.g., using natural language processing, image processing, etc.) medical data to identify a medical condition of a user. The medical management application 160 can further be configured to receive object data of objects in a vicinity of the user. The objects can be analyzed to determine identities and characteristics (e.g., via image processing or natural language processing) of each object such that they can be compared to medical tools used to address the user's medical condition. In embodiments, the comparison of object(s) to medical tool(s) can be completed using an ontology mapping characteristics between objects and medical tools. The medical management application 160 can identify, based on the identified condition, a medical procedure utilizing objects matched to medical tools. The medical management application 160 can then be configured to transmit the procedure to a user including a recommendation that the objects can be used to implement the medical procedure.

In embodiments, the medical management application 160 can monitor the medical condition over time. For example, the medical management application 160 can be configured to prompt the user to provide additional medical data regarding their medical condition after initial support is provided. Based on changes that occur in the medical condition, the medical management application 160 can be configured to issue one or more additional medical treatment recommendations.

In embodiments, the medical management application 160 can be configured to advise a user regarding potential dangers in their environment. The medical management application 160 can indicate these dangers and potential recommendations for addressing potential dangers. This can be completed when object identification is performed to identify objects to be used as medical tools.

In some embodiments, the medical management system can be configured to identify objects that match to respective medical tools and thereafter search for a medical procedure utilizing the objects matching to medical tools. In some embodiments, the medical management system can be configured to identify a medical procedure and thereafter search for objects matching to medical tools to be used to carry out the medical procedure.

Though this disclosure pertains to the collection of personal data (e.g., medical data, object data, etc.), it is noted that in embodiments, users opt-in to the system (e.g., the medical management application 160). In doing so, they are informed of what data is collected and how it will be used, that any collected personal data may be encrypted while being used, that users can opt-out at any time, and that if they opt-out, any personal data of the user is deleted.

It is noted that FIG. 1 is intended to depict the representative major components of an example computing environment 100. In some embodiments, however, individual components can have greater or lesser complexity than as represented in FIG. 1, components other than or in addition to those shown in FIG. 1 can be present, and the number, type, and configuration of such components can vary.

While FIG. 1 illustrates a computing environment 100 with a single server 135, suitable computing environments for implementing embodiments of this disclosure can include any number of servers. The various models, modules, systems, and components illustrated in FIG. 1 can exist, if at all, across a plurality of servers and devices. For example, some embodiments can include two servers. The two servers can be communicatively coupled using any suitable communications connection (e.g., using a WAN, a LAN, a wired connection, an intranet, or the Internet).

Figure 2:
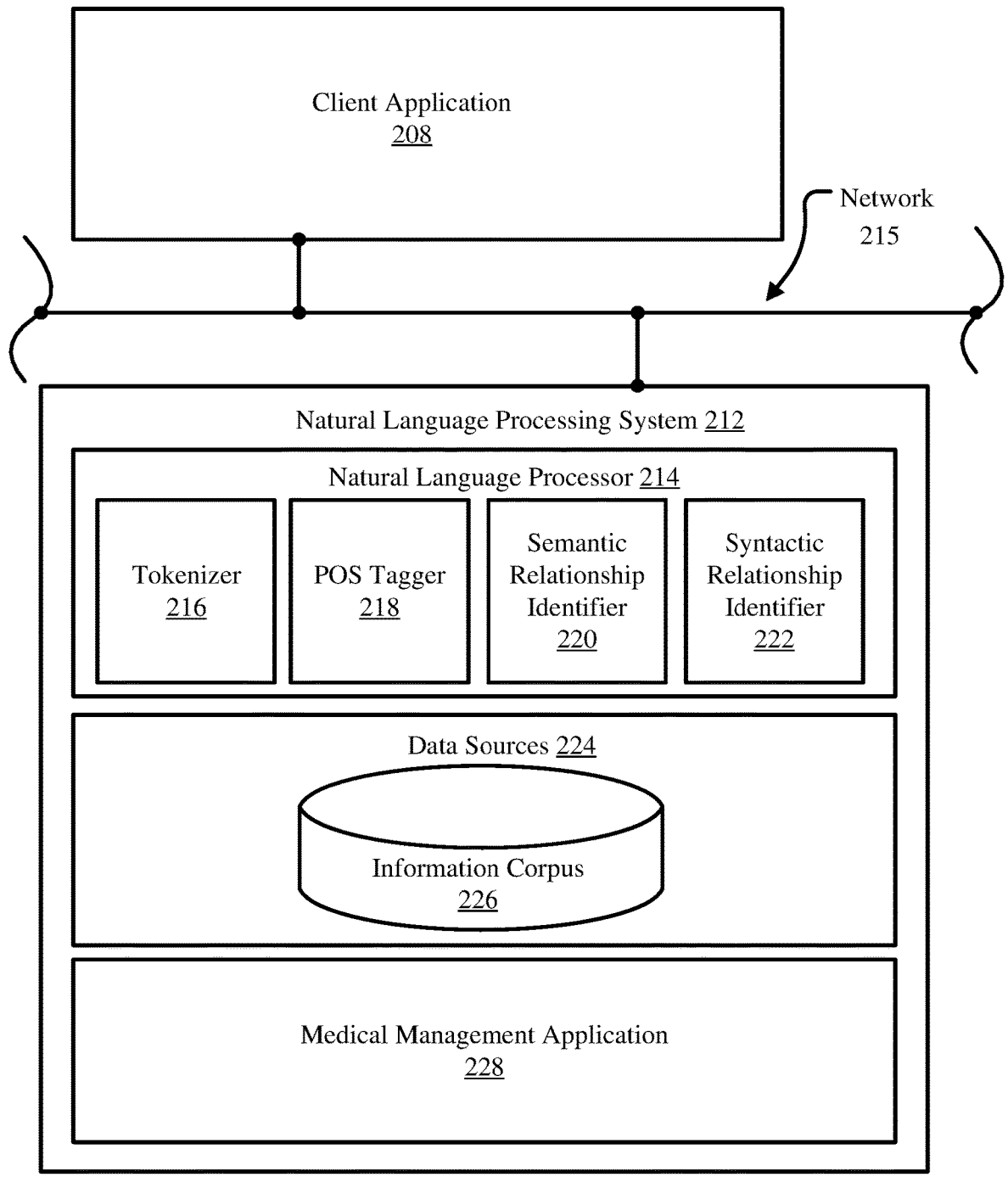
FIG. 2 is a block diagram illustrating a natural language processing system configured to process unstructured data inputs, in accordance with embodiments of the present disclosure.

Turning now to FIG. 2, illustrated is a block diagram of an example natural language processing system 212 configured to process unstructured data inputs (e.g., unstructured text documents), in accordance with embodiments of the present disclosure. In some embodiments, a remote device (e.g., device 105-1 of FIG. 1) can submit input data to be analyzed by the natural language processing system 212, which can be a standalone device, or part of a larger computer system (e.g., server 135). The natural language processing system 212 can include a client application 208, which can itself involve one or more entities operable to generate or modify unstructured input data that is then dispatched to the natural language processing system 212 via a network 215.

Consistent with various embodiments, the natural language processing system 212 can respond to electronic document submissions sent by a client application 208. Specifically, the natural language processing system 212 can analyze a received unstructured data input (e.g., a written description of a medical condition, medical records, a list of objects with corresponding characteristics, a write-up of a medical protocol, etc.) such that the unstructured data input can be considered when issuing medical support recommendations.

The natural language processor 214 can be a computer module that analyzes the received unstructured input data from data sources 224 (e.g., web servers, client devices, storage area networks, medical databases, etc.). In some embodiments, the data sources 224 can include an information corpus 226. The information corpus 226 can enable data storage and retrieval. In some embodiments, the information corpus 226 may be a storage mechanism that houses a standardized, consistent, clean, and integrated list of data that has been arranged subject to data quality or data hygiene systems or rules.

The natural language processor 214 can perform various methods and techniques for analyzing electronic documents (e.g., syntactic analysis, semantic analysis, etc.). The natural language processor 214 can be configured to recognize and analyze any number of natural languages. In some embodiments, the natural language processor 214 can parse passages of the documents. Further, the natural language processor 214 can include various modules to perform analyses of electronic documents. These modules can include, but are not limited to, a tokenizer 216, a part-of-speech (POS) tagger 218, a semantic relationship identifier 220, and a syntactic relationship identifier 222.

In some embodiments, the tokenizer 216 can be a computer module that performs lexical analysis. The tokenizer 216 can convert a sequence of characters into a sequence of tokens. A token can be a string of characters included in an electronic input document and categorized as a meaningful symbol. Further, in some embodiments, the tokenizer 216 can identify word boundaries in an electronic document and break any text passages within the document into their component text elements, such as words, multiword tokens, numbers, and punctuation marks. In some embodiments, the tokenizer 216 can receive a string of characters, identify the lexemes in the string, and categorize them into tokens.

Consistent with various embodiments, the POS tagger 218 can be a computer module that marks up a word in passages to correspond to a particular part of speech. The POS tagger 218 can read a passage or other text in natural language and assign a part of speech to each word or other token. The POS tagger 218 can determine the part of speech to which a word (or other text element) corresponds, based on the definition of the word and the context of the word. The context of a word can be based on its relationship with adjacent and related words in a phrase, sentence, or paragraph. In some embodiments, the context of a word can be dependent on one or more previously analyzed data inputs (e.g., the context of a word in a dictionary can describe or bring further meaning to a word or phrase in an encyclopedia). In embodiments, the output of the natural language processing system 212 can populate a text index, a triple store, or a relational database (RDB) to enhance the contextual interpretation of a word or term. Examples of parts of speech that can be assigned to words include, but are not limited to, nouns, verbs, adjectives, adverbs, and the like. Examples of other part of speech categories that POS tagger 218 can assign include, but are not limited to, comparative or superlative adverbs, wh-adverbs, conjunctions, determiners, negative particles, possessive markers, prepositions, wh-pronouns, and the like. In some embodiments, the POS tagger 218 can tag or otherwise annotate tokens of a passage with part of speech categories. In some embodiments, the POS tagger 218 can tag tokens or words of a passage to be parsed by the natural language processing system 212.

In some embodiments, the semantic relationship identifier 220 can be a computer module that can be configured to identify semantic relationships of recognized text elements (e.g., words, phrases) in documents. In some embodiments, the semantic relationship identifier 220 can determine functional dependencies between entities and other semantic relationships.

Consistent with various embodiments, the syntactic relationship identifier 222 can be a computer module that can be configured to identify syntactic relationships in a passage composed of tokens. The syntactic relationship identifier 222 can determine the grammatical structure of sentences such as, for example, which groups of words are associated as phrases and which word is the subject or object of a verb. The syntactic relationship identifier 222 can conform to formal grammar.

In some embodiments, the natural language processor 214 can be a computer module that can parse a document and generate corresponding data structures for one or more portions of the document. For example, in response to receiving an unstructured textual report at the natural language processing system 212, the natural language processor 214 can output parsed text elements from the report as data structures. In some embodiments, a parsed text element can be represented in the form of a parse tree or other graph structure. To generate the parsed text element, the natural language processor 214 can trigger computer modules 216-222.

In embodiments, the output of natural language processor 214 can be used by a medical management application 228 (e.g., medical management application 160 of FIG. 1). By converting unstructured medical data into a structured format, the medical management application 228 can aid in providing medical support to a user. For example, the natural language processor 214 can aid in identifying a condition based on unstructured textual data, identifying objects based on unstructured textual data, and identifying medical procedures used to address the medical condition using unstructured textual data. In embodiments, the medical management application 228 can transmit a medical procedure including a recommendation that objects (e.g., articles of clothing, a razor blade, car parts, travel gear, etc.) matching respective medical tools (e.g., bandages, scalpel, crutches, etc.) can be used to implement the medical procedures.

As discussed above, the output of the natural language processor 214 can be used by the medical management application 228 to identify a medical condition. For example, the natural language processor 214 can convert unstructured medical data (e.g., a written description of a condition) into a structured format such that the medical management application 228 can identify the condition (e.g., by comparing characteristics of the medical condition to known medical conditions within a medical database).

The output of the natural language processor 214 can also be used by the medical management application 228 to identify and characterize objects. For example, the natural language processor 214 can convert unstructured textual object data (e.g., a written description of an object) into a structured format such that the medical management application 228 can ascertain an identity and/or characteristics of the object. In some embodiments, the structured written description of the object can be compared to an online database to aid in identifying and/or further characterizing the object. For example, a name, product number, serial number, or bar code of an object can be compared with an online database to identify a product specification or description corresponding to the object.

Figure 3:
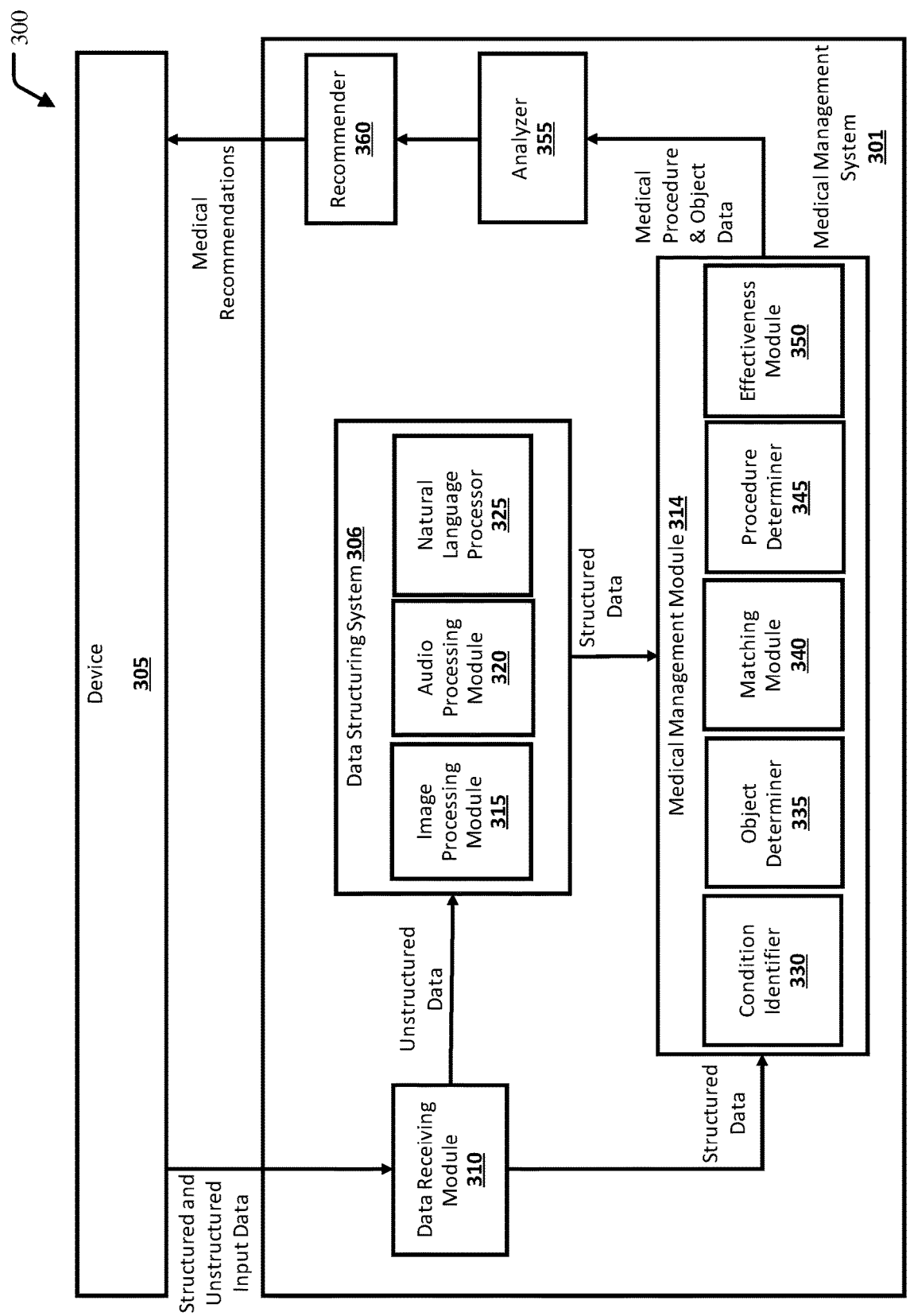
FIG. 3 is a block diagram illustrating an example computing environment including a medical management system, in accordance with embodiments of the present disclosure.

FIG. 3 is a block diagram illustrating an example computing environment 300 in which illustrative embodiments of the present disclosure can be implemented. The computing environment 300 includes a device 305 and a medical management system 301. The medical management system 301 includes a data receiving module 310, a data structuring system 306, a medical management module 314, an analyzer 355, and a recommender 360. In embodiments, the data receiving module 310, data structuring system 306, medical management module 314, analyzer 355, and recommender 360 can be processor executable instructions that can be executed by a dedicated or shared processor using received inputs (e.g., from device 305).

Consistent with various embodiments, the data receiving module 310 can be configured to receive input data from the device 305. The device 305 (e.g., devices 105 of FIG. 1) can transmit various structured and unstructured data (e.g., images, electronic documents, videos, audio records, websites, etc.) to the data receiving module 310. In some embodiments, the structured and unstructured data can be received from a plurality of devices (e.g., in a distributed computing environment). The input data can be transmitted to the data receiving module 310 in any manner. For example, in some embodiments, input data is transmitted over a network (e.g., network 150 of FIG. 1 or network 215 of FIG. 2). The data can be received as pushed by the device 305, or alternatively, as pulled by the data receiving module 310.

After the input data is received, it can be organized into a structured data portion and an unstructured data portion. The data receiving module 310 can include logic to differentiate between structured and unstructured data. For example, in some embodiments, the data receiving module 310 only transmits data of a particular format (e.g., pdf, word, html, jpeg, etc.) to the medical management module 314. After the data is organized into an unstructured portion and a structured portion, the unstructured data portion is transmitted to the data structuring system 306, and the structured data portion is transmitted to the medical management module 314.

The data structuring system 306 is configured to structure the unstructured data received from the data receiving module 310. The unstructured data can include images, videos, electronic text documents, audio clips, etc. An image processing module 315, audio processing module 320, and natural language processor 325 (e.g., natural language processor 214 of FIG. 2) are configured to structure the data.

The image processing module 315 can be configured to perform various image analysis techniques. The image analysis techniques can be machine learning and/or deep learning based techniques. These techniques can include, but are not limited to, region-based convolutional neural networks (R-CNN), you only look once (YOLO), edge matching, clustering, grayscale matching, gradient matching, invariance models, geometric hashing, scale-invariant feature transform (SIFT), speeded up robust feature (SURF), histogram of oriented gradients (HOG) features, and single shot multibox detector (SSD). In embodiments, the image processing module 315 can be configured to aid in identifying a medical condition (e.g., by analyzing images of a condition using a model built on training data). In embodiments, the image processing module 315 can perform object recognition to aid in identifying and/or characterizing objects in a vicinity of a user. The output of the image processing module 315 can include a classification of one or more objects within an image with corresponding match certainties. In some embodiments, the image processing module 315 can be configured to extract text from images (e.g., extract a particular object name from text on an object). An example image recognition tool is IBM Watson™ Visual Recognition.

The audio processing module 320 can be configured to generate text from audio inputs using speech to text (STT) techniques. These techniques can be based on Hidden Markov Models (HMMs), dynamic time warping (DTW), neural networks, end-to-end automatic speech recognition, and others. For example, for a given audio clip, the audio processing module 320 can be configured to detect speech and convert the speech into text. An example of an audio processing tool is IBM Watson™ Speech to Text. The text can then be forwarded to the natural language processor 325 for analysis.

In embodiments, the output of the audio processing module 320 can be analyzed for tonal and/or emotional features. For example, the text output from the audio processing module 320 can be analyzed to ascertain emotions (e.g., happy, sad, confident, etc.) within the text. An example of a tone/emotion analyzer is IBM Watson™ Tone Analyzer.

In some embodiments, the image processing module 315 and audio processing module 320 are configured to cooperatively process video inputs. For example, the audio processing module 320 can be configured to process audio from the video input, while the image processing module 315 can be configured to process frames of the video input.

The natural language processor 325 receives unstructured textual input data (e.g., directly from data receiving module 310 or from processing modules 315 and/or 320) and structures the textual input data. In some embodiments, the textual input data is structured into a format readable by the medical management module 314. The natural language processor 325 can be configured to perform one or more of the natural language processing techniques described with respect to the natural language processing system 212 of FIG. 2. An example of a natural language processing tool is IBM Watson™ Natural Language Understanding.

The medical management module 314 receives structured data from the data receiving module 310 and/or data structuring system 306. The medical management module 314 includes a condition identifier 330, an object determiner 335, a matching module 340, a procedure determiner 345, and an effectiveness module 350. In embodiments, the condition identifier 330, the object determiner 335, the matching module 340, the procedure determiner 345, and the effectiveness module 350 can be processor executable instructions that can be executed by a dedicated or shared processor using received inputs (e.g., from device 305).

The condition identifier 330 can be configured to identify a medical condition of an individual. For example, the user may submit various structured and/or unstructured input data such as images (e.g., a picture of a cut, rash, bruise, etc.), text documents (e.g., a written description of the symptoms the user is experiencing), and/or audio/video (AV) recordings (e.g., an utterance describing the medical condition by a user) to the medical management system 301. The medical condition can then be identified based on the received input data (received from the data structuring system 306 or alternatively, directly from the data receiving module 310).

The medical condition can be identified in any suitable manner. For example, the medical condition can be identified by matching characteristics of the condition (e.g., obtained from an image, a written description, or an oral description of the condition) to known medical conditions within a website, medical database, or any other source. In embodiments, a threshold number of matching characteristics between the medical condition and a known medical condition can be used to determine whether there is a match. For example, if a user snaps a picture of a rash, three characteristics can be used to determine whether the rash matches a known condition. These conditions may be size, shape, and color. If the size, shape, and color, of the rash matches a known condition within a medical database, the known condition can be identified as the medical condition.

In some embodiments, the condition identifier 330 can identify the medical condition with the aid of a supervised learning model built on training data. For example, an image of a medical condition can be input into a machine learning model such that it can be identified using a library of pre-classified images of the condition.

In some embodiments, the medical condition can be identified with the aid of an expert. That is, the medical data associated with the user (e.g., the image of the condition, the written description of the condition, etc.) can be forwarded to an expert (e.g., a medical doctor) by the condition identifier 330 such that the expert can aid in identifying the medical condition. The feedback received from the expert can then be received and used to identify the medical condition by the condition identifier 330.

The identity of the medical condition can then be transmitted to the procedure determiner 345 such that the procedure determiner 345 can identify one or more procedures which can be used to address the medical condition.

The object determiner 335 can be configured to identify and characterize objects within an individual's environment. This is completed such that objects can be matched to medical tools and used when attempting to treat the medical condition. For example, a user may submit various structured and/or unstructured input data such as images (e.g., a picture of a stone, razor blade, shirt, etc.), text documents (e.g., a written description of objects in the vicinity), and/or audio/video (AV) recordings (e.g., an utterance describing the objects in the vicinity) to the medical management system 301. The object determiner 335 can analyze this input data to determine the identity and/or characteristics of objects in a vicinity of the user. The identity and/or characteristics of objects can be used to match the objects to medical tools by the matching module 340.

The object determiner 335 can be configured to identify and/or characterize objects in any suitable manner. The identity of objects can be determined with the aid of image processing techniques (e.g., completed by the image processing module 315), audio processing techniques (e.g., completed by the audio processing module 320), and/or natural language processing techniques (e.g., completed by the natural language processor 325).

In embodiments, the object determiner 335 can identify and/or characterize objects using image analysis techniques (e.g., deep learning, clustering, supervised machine learning, unsupervised machine learning, etc.). To do so, the object determiner 335 can receive an image including one or more objects in a vicinity of a user. The image can then be analyzed, using various techniques described with respect to the image processing module 315 such that an identity and/or characteristics of respective objects can be determined.

In some embodiments, objects can be identified using an object detection algorithm, such as an R-CNN, YOLO, SSD, SIFT, Hog features, or other machine learning and/or deep learning object detection algorithms. The output of the object detection algorithm can include one or more identities of one or more respective objects with corresponding match certainties.

In some embodiments, an identity and/or characteristics of objects can be determined using a supervised machine learning model built using training data. For example, an image can be input into the supervised machine learning model and various classifications detected within the image can be output by the model. For example, characteristics such as object material (e.g., cloth, metal, plastic, etc.), shape, size, color, and other characteristics can be output by the supervised machine learning model. Further, the identification of objects (e.g., a shoe, a rock, a head rest, etc.) can be output as classifications determined by the supervised machine learning model. For example, if a user snaps an image of their vehicle, a supervised machine learning algorithm can be configured to output an identity of the object (e.g., automobile) as well as various characteristics of their vehicle (e.g., the model, make, color, etc.).

In some embodiments, characteristics of objects can be determined using photogrammetry techniques. For example, shapes and dimensions of objects can be approximated using photogrammetry techniques. As an example, if a user provides an image of a basket, the diameter, depth, thickness, etc. of the basket can be approximated using photogrammetry techniques.

In embodiments, the object determiner 335 can determine characteristics of objects by referencing an ontology. For example, if an object is identified (e.g., using an R-CNN), the identity of the object can be referenced within an ontology to determine corresponding attributes of the object. The ontology can indicate attributes such as color, size, shape, use, etc. of the object.

In embodiments, the object determiner 335 can be configured to characterize an object by referencing an online database (e.g., a manufacturer website and/or market place). For example, based on the identity of the object (e.g., a product number, serial number, product name, etc. of an object), an online product description and/or specification can be referenced to determine characteristics of the object. For example, a product specification can indicate a weight of an object, dimensions of an object, parts or components within an object, an intended use of an object, etc.

In some embodiments, object identities and/or object characteristics can be determined via audio processing techniques. For example, an individual (or entity such as a voice command device (VCD)) may utter a name, description, serial number, or other identifier of an object into a microphone of their device (e.g., device 305). The data receiving module 310 can then receive the speech, and the speech can be converted to a structured text format by the audio processing module 320. The text can then be analyzed to ascertain an identity and/or characteristics of the object. For example, the identity and/or characteristics of the objects can be explicitly indicated within the text. In some embodiments, the object can be referenced against an online database to determine the characteristics of the object.

In embodiments, the identity of an object can be determined via natural language processing. For example, a user may submit an unstructured electronic document (e.g., from device 305) containing a list of various objects discovered in the surrounding area to the data receiving module 310. In some embodiments, the unstructured electronic document may explicitly indicate characteristics of the various objects. The natural language processor 325 can then be configured to process the electronic document such that the object determiner 335 can determine the characteristics and/or identity of various objects within the text document. In some embodiments, structured text can be referenced against an online database for further identification and/or characterization.

The output of the object determiner 335 can include identities and/or characteristics of objects in the area surrounding the user. Characteristics can include the shapes of objects, dimensions (e.g., height, length, and width) of objects, a number of objects, colors of object, and/or other attributes of objects. In some embodiments, the object determiner 335 can output a list including the identity and/or characteristics of objects (e.g., cotton shirt, serrated knife, etc.).

In embodiments, the object determiner 335 can output an indication that an identity or characteristic of an object is unknown. In these instances, the object determiner 335 can request additional input data to be analyzed such that the identity and/or characteristics of objects can be ascertained. For example, if a user inputs an image of a surrounding area that includes objects that cannot be recognized by the medical management system 301, the user can be prompted to provide additional input data such that objects in their surrounding can be recognized.

In embodiments, the object determiner 335 can be used to identify potential dangers in an area surrounding the user. For example, a list storing identities and/or characteristics of objects can be referenced against a datastore containing a list of potential dangers (e.g., a snake, scorpion, cliff edge, etc.). If there is a match between any objects on the object list and any items on the list of potential danger list, a warning can be transmitted to the user.

The matching module 340 can be configured to receive the object data from the object determiner 335 and compare the object data to medical tools (e.g., stored in a medical database). The object data is compared to medical tools to identify a match between one or more objects and respective medical tools. As discussed herein, a "match" between an object and a medical tool may not be an exact match. The match between the object and medical tool can depend on a matching algorithm used to compare the object to the medical tool. In some embodiments, a match can be determined based on a threshold number of shared characteristics between an object and a medical tool. In some embodiments, a match can denote that an object and medical tool are substantially similar. Further, a "medical tool" can include any suitable tool used to treat a medical condition, and does not necessarily have to be found in a hospital/medical setting. For example, medical tools can include items such as gloves, filters, needles, screws, wires, clamps, tubing, sutures, pins, rods, knives, etc.

In some embodiments, the matching module 340 matches characteristics of objects to characteristics of medical tools via an ontology. For example, various objects, object attributes, and relationships between objects (e.g., hierarchical and direct relations) can be represented within a knowledge graph (KG) structure. The relationships between objects and medical tool objects within the KG can be leveraged when matching objects to medical tools. For example, objects can be matched to medical tools based on shared characteristics (e.g., both the object and medical tool are sharp), relationships with other objects (e.g., both the object and medical tool have a handle), or objects belonging to the same class (e.g., both the object and medical tool belong to a drug class "analgesics").

In embodiments, a threshold number of matching characteristics are used to determine whether there is match. For example, an object, object 1 (e.g., a razor blade), can be matched with a medical tool, medical tool 1 (e.g., a scalpel), based on a number of matching characteristics (e.g., sharp, metal, has handle) shared within an ontology. In response to the number of matching characteristics satisfying a match threshold, a match between the object and medical tool can be confirmed by matching module 340. The objects matching to medical tools can be stored for later use when determining a medical procedure to be used to address the condition.

The procedure determiner 345 can be configured to determine one or more medical procedures which can be used to treat the medical condition indicated by the condition identifier 330. In embodiments, the medical condition data can be referenced against a database storing medical procedures. The procedure determiner 345 can be configured to determine appropriate medical procedures to address the medical condition by parsing text within the medical procedure database. For example, medical procedures typically describe the condition and/or symptoms they are intended to address. As such, the procedure determiner 345 can identify keywords within the medical procedure database that indicate a relationship between a particular medical procedure and a particular medical condition. For example, if the procedure determiner 345 identifies a phrase such as "Medical Procedure A can be used to alleviate Condition B," then, if Condition B was identified by the condition identifier 330, Medical Procedure A can be selected by the procedure determiner 345 as a potential candidate procedure used to address Condition B.

In some embodiments, the medical condition can be analyzed by a medical expert (e.g., a medical doctor) to determine an appropriate medical procedure. For example, the procedure determiner 345 can be configured to prompt a medical expert regarding suitable procedures to treat a medical condition. The procedure determiner 345 can then receive the recommendation from the medical expert as a potential medical procedure used to treat the medical condition.

In embodiments, the procedure determiner 345 can be configured to output an indication that no suitable medical procedures used to address the medical condition were identified. In these embodiments, the medical management system 301 can be configured to request additional input data (e.g., data describing the user's condition and/or additional medical procedure data) such that an appropriate medical procedure can be determined.

The effectiveness module 350 can be configured to receive user feedback regarding determinations made by the condition identifier 330, object determiner 335, matching module 340, and procedure determiner 345. This feedback can be used to improve the identification of conditions, the determination and/or characterization of objects, the matching of objects to medical tools, and the determination of a medical procedure that can be used to address the medical condition. For example, the effectiveness module 350 can issue positive or negative feedback (e.g., reinforcement learning) to the condition identifier 330, object determiner 335, matching module 340, and/or procedure determiner 345 based on a comparison between the determinations and observed results.

The effectiveness module 350 can be configured to improve condition identification. Based on the difference between the identified condition (e.g., determined by the condition identifier 330) and an expected medical condition (e.g., manually defined by an expert), feedback can be issued by the effectiveness module 350 to improve prediction accuracy. For example, assume the condition was identified as a broken leg by the condition identifier 330. The effectiveness module 350 can then be configured to receive training data from an expert regarding the condition determination. In this example, the expert may determine that the condition is not a broken leg, but rather a leg sprain. Based on the inaccurate approximation by the condition identifier 330, negative feedback can be issued to the condition identifier 330. In contrast, if the prediction was accurate, positive reinforcement could be issued to the condition identifier 330.

In embodiments, the effectiveness module 350 can be configured to improve identification and characterizations of objects made by the object determiner 335. For example, assume the total length of an object was determined to be 5 in. The effectiveness module 350 can then be configured to receive a user measurement of the object. Based on the difference between the estimation and the actual measurement, a feedback signal can be provided to the object determiner 335. For example, if the prediction was incorrect by a particular margin (e.g., 2 in.), negative feedback could be issued to the object determiner 335. In contrast, if the prediction was within a particular margin, positive reinforcement could be issued to the object determiner 335. This feedback can be used to improve the accuracy of the object determiner 335 over time. The feedback (e.g., whether the feedback is positive or negative, the magnitude of the feedback, etc.) issued by the effectiveness module 350 can depend on the difference between approximated object characteristics and the observed (e.g., measured) object characteristics.

In embodiments, the effectiveness module 350 can be configured to issue feedback to the procedure determiner 345 based on the effectiveness of the treatment. For example, if the medical procedure did not successfully treat the medical condition and/or lead to negative side effects, negative feedback could be issued to the procedure determiner 345. Conversely, if the medical procedure successfully treated the medical condition with no side effects, positive feedback could be provided to the procedure determiner 345.

The analyzer 355 is configured to analyze the data received from the medical management module 314. The analyzer 355 can be configured to receive the object data of the objects matching to medical tools (e.g., determined by object determiner 335 and matching module 340) and the medical procedure(s) (e.g., determined by the procedure determiner 345) to determine whether the matching objects (objects which are determined to be substantially similar to tools) can be used to carry out a procedure. For example, the analyzer 355 can determine if a procedure can be used based on that availability of objects that can be used as tools to carry out the procedure. The output of the analyzer 355 can include one or more procedure recommendations as well as matching objects to carry out the one or more procedures to be issued by the recommender 360.

In embodiments, the analyzer 355 can generate a formatted document (e.g., an electronic document) based on the output of the medical management module 314, and the formatted document can be transmitted to the device 305 by the recommender 360. For example, in some embodiments, analyzer 355 can superimpose images of the medical tools mapped to objects on top of the objects within the images received from the user. Further, the medical procedure utilizing the medical tools can be appended to the formatted document.

As an example, an image received from a user can include a knife which was mapped to a scalpel. In this example, the scalpel can be superimposed on the image of the knife. Further, step-by-step instructions for carrying out the procedure utilizing the scalpel can be appended to the document. This provides the user with an easily understandable document for carrying out the medical procedure, as well as clear mappings of objects to medical tools. In some embodiments, the formatted document can simply include the medical procedure as determined by the procedure determiner 345 with matching objects replacing text of corresponding medical tools within the procedure. For example, if a procedure reads "Make a 5 cm incision 2 cm deep with the scalpel," the formatted document produced by the analyzer 355 could read "Make a 5 cm incision 2 cm deep with the knife."

In embodiments, if a determination is made that there are insufficient matching objects to carry out a procedure, then the analyzer 355 can be configured determine that more data is needed. In these embodiments, the recommender 360 can prompt the user to provide additional object data. For example, if a procedure requires a bandage and no objects match to a bandage (e.g., no object is substantially similar to a bandage or no object has a threshold number of matching characteristics with a bandage), the analyzer 355 can determine that there is insufficient data, and the recommender 360 can prompt the user to provide additional data.

Reference will now be made to a detailed example of a medical recommendation provided by the medical management system 301. In this example, input data received from a user can include an image of a raised bump on the skin provided by the user (e.g., via device 305). The condition identifier 330 can first be configured to identify the medical condition the user is experiencing. In this example, the condition identifier 330 can be configured to match characteristics of the raised bump to characteristics of known medical conditions. For example, the medical condition can be identified as "spider bite" based on the size of the bump, color of the bump, and puncture marks of the bite matching characteristics of the known condition "spider bite." Upon identifying the condition, the condition identifier 330 transmits the condition to the procedure determiner 345. The procedure determiner 345 then determines a medical procedure used to address the condition "spider bite." In this example, the procedure determiner 345 outputs a procedure including two steps according to a medical database:

1. Clean the area of the bite with soap and water; and
2. Apply ice to the area of the bite on and off for 10 minute periods Upon receiving the procedure, the user captures images of their surrounding area and transmits the images to the medical management system 301. The object determiner 335 then identifies and outputs a list of objects with corresponding characteristics. The list of objects is then matched to medical tools by the matching module 340 using the characteristics. The matching module 340 outputs various objects that match to medical tools, including two objects needed for the procedure: "Frozen Vegetables" located in a cooler matching to "Ice" and "Hand Sanitizer" found on a table matching to "Soap and Water". The analyzer 355 then determines that the objects "Frozen Vegetables" and "Hand Sanitizer" can be used to implement the two-step medical procedure. The recommender 360 receives this determination from the analyzer 355, and transmits a recommendation that the user should complete the following two-step medical procedure:

1. Sanitize the area of the bite with Hand Sanitizer; and
2. Apply Frozen Vegetables to the area of the bite on and off for 10 minute periods The recommendation can then be received by the device 305 and displayed on a graphical user interface (GUI) such that the user can carry out the procedure with the tools on hand. The medical management system 301 then awaits further input data and/or feedback from the user regarding updates to their current condition and/or any new conditions.

It is noted that FIG. 3 is intended to depict the representative major components of an example computing environment 300. In some embodiments, however, individual components can have greater or lesser complexity than as represented in FIG. 3, components other than or in addition to those shown in FIG. 3 can be present, and the number, type, and configuration of such components can vary. For example, in some embodiments, the medical management system 301 may not include an audio processing module 320, as the medical management system 301 may not be configured to receive audio data.

Figure 4:
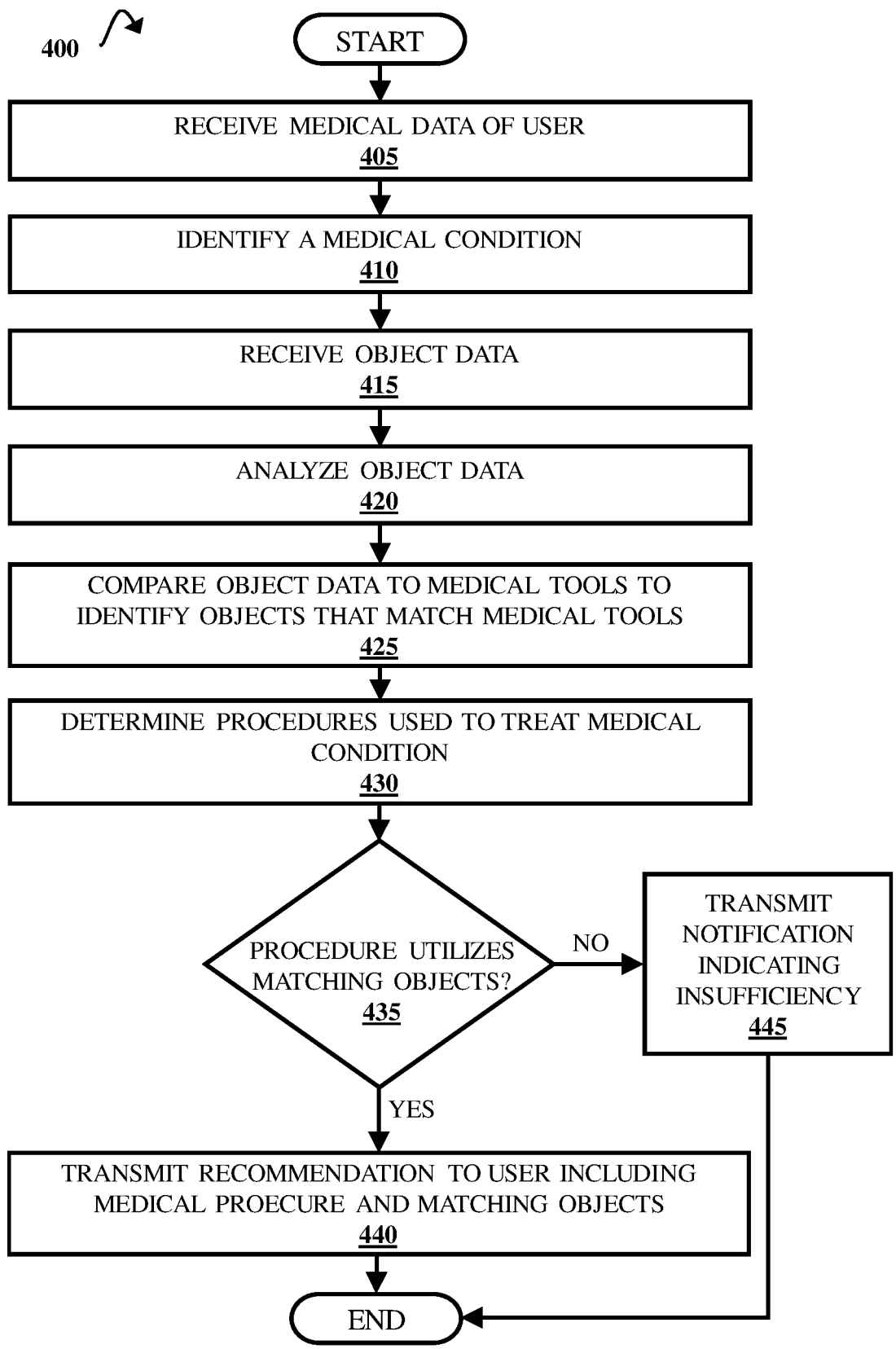
FIG. 4 is flow-diagram illustrating an example method for determining whether a recommendation should be issued, in accordance with embodiments of the present disclosure.

FIG. 4 is a flow diagram illustrating an example method 400 for providing medical support to a user, in accordance with embodiments of the present disclosure. Method 400 initiates at operation 405, where the medical data is received. Medical data can include various data related to a medical condition provided by a user. For example, medical data can include images of a condition, text describing a condition, or an audio/video description of a condition. This data can then be processed and analyzed (e.g., by the data structuring system 306 and condition identifier 330). Medical data can be received in any suitable manner. For example, the medical data can be received over a network, using a wireless link, or using a wired connection.

A medical condition is then identified based on an analysis of the medical data of the user. This is illustrated at operation 410. In embodiments, the medical condition can be identified using the same, or substantially similar, techniques described with respect to the condition identifier 330 of FIG. 3. For example, the medical condition can be identified using a supervised machine learning model or based on a number of shared characteristics between the condition and a known condition. The output of the condition identification can include one or more potential medical condition approximations.

Object data is then received. This is illustrated at operation 415. Object data can include images, written descriptions, and/or audio/video descriptions of objects in a vicinity of a user. The object data can then be processed and analyzed (e.g., by the data structuring system 306 and object determiner 335). Object data can be received in any suitable manner. For example, the object data can be received over a network, using a wireless link, or using a wired connection.

At operation 420, object data is analyzed. Object data can be analyzed in any suitable manner. Object data can be analyzed in the same, or a substantially similar, manner as described with respect to the object determiner 335 of FIG. 3. For example, objects within the object data can be identified and/or characterized using image processing techniques (e.g., deep learning, clustering, supervised machine learning, unsupervised machine learning, etc.). The output of the object analysis can include a list of objects and corresponding characteristics.

Object data is then compared to medical tools to identify objects that match medical tools. This is illustrated at operation 425. In embodiments, objects can be compared to medical tools using an ontology. For example, shared attributes and/or relationships between objects can be used to determine whether the object matches a particular medical tool object within an ontology. In some embodiments, objects can be matched based on a threshold number of shared characteristics between objects and medical tools. The matching of objects to medical tools can be completed in the same, or a substantially similar, manner as described with respect to the matching module 340 of FIG. 3.

A medical procedure used to address the medical condition is then determined. This is illustrated at operation 430. Determining the medical procedure can be completed in the same, or a substantially similar, manner as described with respect to the procedure determiner 345 of FIG. 3. For example, the medical procedure can be determined by parsing a medical procedure database for keywords related to the condition.

A determination is made whether the procedure can be completed by utilizing the matching objects. This is illustrated at operation 435. For example, if a medical procedure requires four medical tools, tool 1, tool 2, tool 3, and tool 4, and only three matching objects are available, matching object 1 (an object that matches to tool 1), matching object 3 (an object that matches to tool 3), and matching object 4 (an object that matches to tool 4), then a determination is made that the procedure cannot be completed utilizing the matching objects. Conversely, if all four tools had corresponding matching objects, a determination would be made that the procedure could be completed utilizing the matching objects.

If a determination is made that the procedure can be completed by utilizing the matching objects, then a recommendation is transmitted to the user including the medical procedure and the matching objects used to carry out the medical procedure. This is illustrated at operation 440. In some embodiments, a formatted document, such as the formatted documents described with respect to FIG. 3, can be transmitted to a user including object to tool matching (e.g., medical tools superimposed on objects or medical tool text replaced with object names with step-by-step instructions for carrying out the procedure).

If a determination is made that the procedure cannot be completed utilizing the matching objects, then a notification indicating the inability to carry out the procedure is transmitted to a user. This is illustrated at operation 445. In some embodiments, the notification can include an indication of one or more missing tools. In some embodiments, objects can be proposed for missing tools which may not have been determined at operations 420-425. For example, if the user is missing a bandage noted within the medical procedure, a recommendation can be transmitted suggesting that the user should attempt to find an object "cloth." In some embodiments, the user can be prompted to provide additional object data (e.g., additional images of their surrounding) such that an object matching to a missing medical tool can be located. Upon transmitting the recommendation at operation 440 or transmitting the notification at operation 445, method 400 ends.

The aforementioned operations can be completed in any order and are not limited to those described. Additionally, some, all, or none of the aforementioned operations can be completed, while still remaining within the spirit and scope of the present disclosure.

Figure 5:
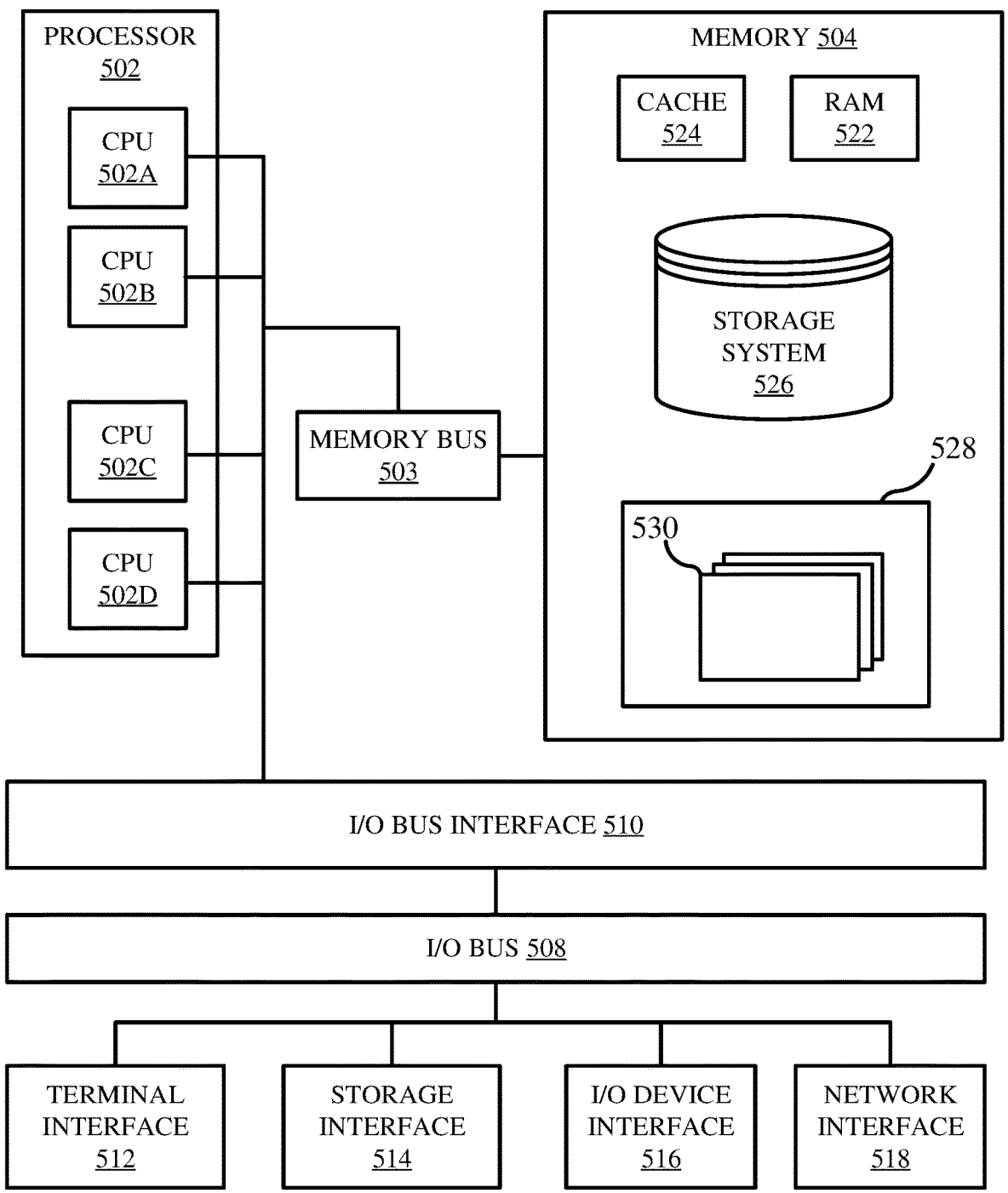
FIG. 5 is a high-level block diagram illustrating an example computer system that can be used in implementing one or more of the methods, tools, and modules, and any related functions described herein, in accordance with embodiments of the present disclosure.

Referring now to FIG. 5, shown is a high-level block diagram of an example computer system 501 that may possibly be utilized in various devices discussed herein (e.g., devices 105, server 135, natural language processing system 212, device 305, medical management system 301) and that may be used in implementing one or more of the methods, tools, and modules, and any related functions, described herein (e.g., using one or more processor circuits or computer processors of the computer), in accordance with embodiments of the present disclosure. In some embodiments, the major components of the computer system 501 may comprise one or more CPUs 502, a memory 504, a terminal interface 512, a storage interface 514, an I/O (Input/Output) device interface 516, and a network interface 518, all of which may be communicatively coupled, directly or indirectly, for inter-component communication via a memory bus 503, an I/O bus 508, and an I/O bus interface unit 510.

The computer system 501 may contain one or more general-purpose programmable central processing units (CPUs) 502A, 502B, 502C, and 502D, herein generically referred to as the CPU 502. In some embodiments, the computer system 501 may contain multiple processors typical of a relatively large system; however, in other embodiments the computer system 501 may alternatively be a single CPU system. Each CPU 502 may execute instructions stored in the memory subsystem 504 and may include one or more levels of on-board cache.

System memory 504 may include computer system readable media in the form of volatile memory, such as random access memory (RAM) 522 or cache memory 524. Computer system 501 may further include other removable/non-removable, volatile/non-volatile computer system storage media. By way of example only, storage system 526 can be provided for reading from and writing to a non-removable, non-volatile magnetic media, such as a "hard-drive." Although not shown, a magnetic disk drive for reading from and writing to a removable, non-volatile magnetic disk (e.g., a "floppy disk"), or an optical disk drive for reading from or writing to a removable, non-volatile optical disc such as a CD-ROM, DVD-ROM or other optical media can be provided. In addition, memory 504 can include flash memory, e.g., a flash memory stick drive or a flash drive. Memory devices can be connected to memory bus 503 by one or more data media interfaces. The memory 504 may include at least one program product having a set (e.g., at least one) of program modules that are configured to carry out the functions of various embodiments.

One or more programs/utilities 528, each having at least one set of program modules 530 may be stored in memory 504. The programs/utilities 528 may include a hypervisor (also referred to as a virtual machine monitor), one or more operating systems, one or more application programs, other program modules, and program data. Each of the operating systems, one or more application programs, other program modules, and program data or some combination thereof, may include an implementation of a networking environment. Programs 528 and/or program modules 530 generally perform the functions or methodologies of various embodiments.

In some embodiments, the program modules 530 of the computer system 501 may include a medical management module. The medical management module can be configured to receive medical data of a user and identify a medical condition based on the medical data. The medical management module can further be configured to determine a medical procedure used to address the medical condition. The medical management module can further be configured to identify and characterize objects within a vicinity of a user, and match the objects to medical tools. A medical procedure utilizing the matching medical tools can then be identified. A recommendation can then be transmitted including the medical procedure and an indication that the matching objects can be used as tools to carry out the medical procedure.

Although the memory bus 503 is shown in FIG. 5 as a single bus structure providing a direct communication path among the CPUs 502, the memory subsystem 504, and the I/O bus interface 510, the memory bus 503 may, in some embodiments, include multiple different buses or communication paths, which may be arranged in any of various forms, such as point-to-point links in hierarchical, star or web configurations, multiple hierarchical buses, parallel and redundant paths, or any other appropriate type of configuration. Furthermore, while the I/O bus interface 510 and the I/O bus 508 are shown as single respective units, the computer system 501 may, in some embodiments, contain multiple I/O bus interface units 510, multiple I/O buses 508, or both. Further, while multiple I/O interface units are shown, which separate the I/O bus 508 from various communications paths running to the various I/O devices, in other embodiments some or all of the I/O devices may be connected directly to one or more system I/O buses.

In some embodiments, the computer system 501 may be a multi-user mainframe computer system, a single-user system, or a server computer or similar device that has little or no direct user interface, but receives requests from other computer systems (clients). Further, in some embodiments, the computer system 501 may be implemented as a desktop computer, portable computer, laptop or notebook computer, tablet computer, pocket computer, telephone, smart phone, network switches or routers, or any other appropriate type of electronic device.

It is noted that FIG. 5 is intended to depict the representative major components of an exemplary computer system 501. In some embodiments, however, individual components may have greater or lesser complexity than as represented in FIG. 5, components other than or in addition to those shown in FIG. 5 may be present, and the number, type, and configuration of such components may vary.

It is to be understood that although this disclosure includes a detailed description on cloud computing, implementation of the teachings recited herein are not limited to a cloud computing environment. Rather, embodiments of the present disclosure are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 6:
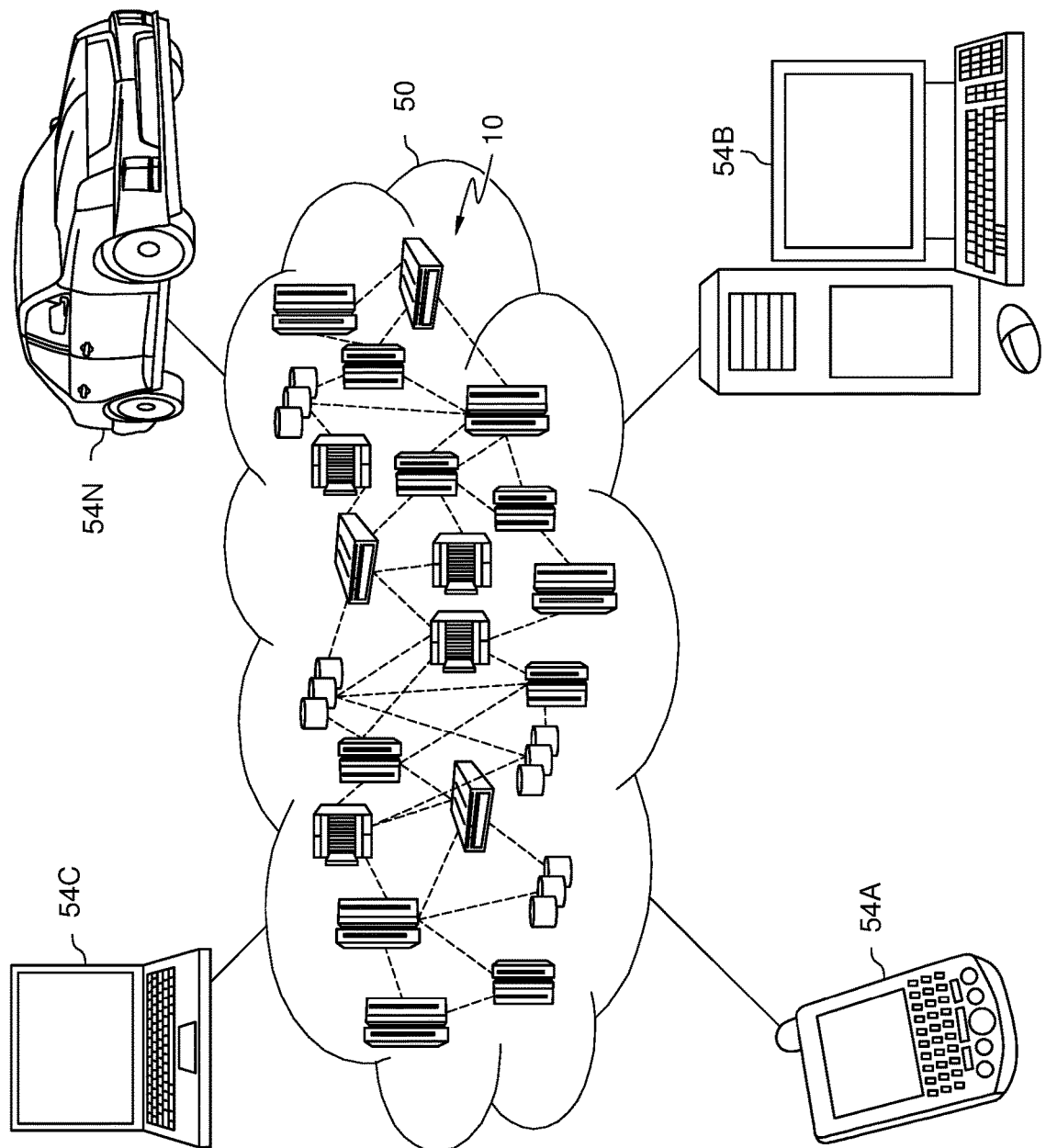
FIG. 6 is a diagram illustrating a cloud computing environment, in accordance with embodiments of the present disclosure.

Referring now to FIG. 6, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A (e.g., devices 105, device 305, etc.), desktop computer 54B (e.g., server 135, medical management system 301), laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 10 and cloud computing environment 50 can communicate with any type of computerized device over any type of network and/or network addressable connection (e.g., using a web browser).

Figure 7:
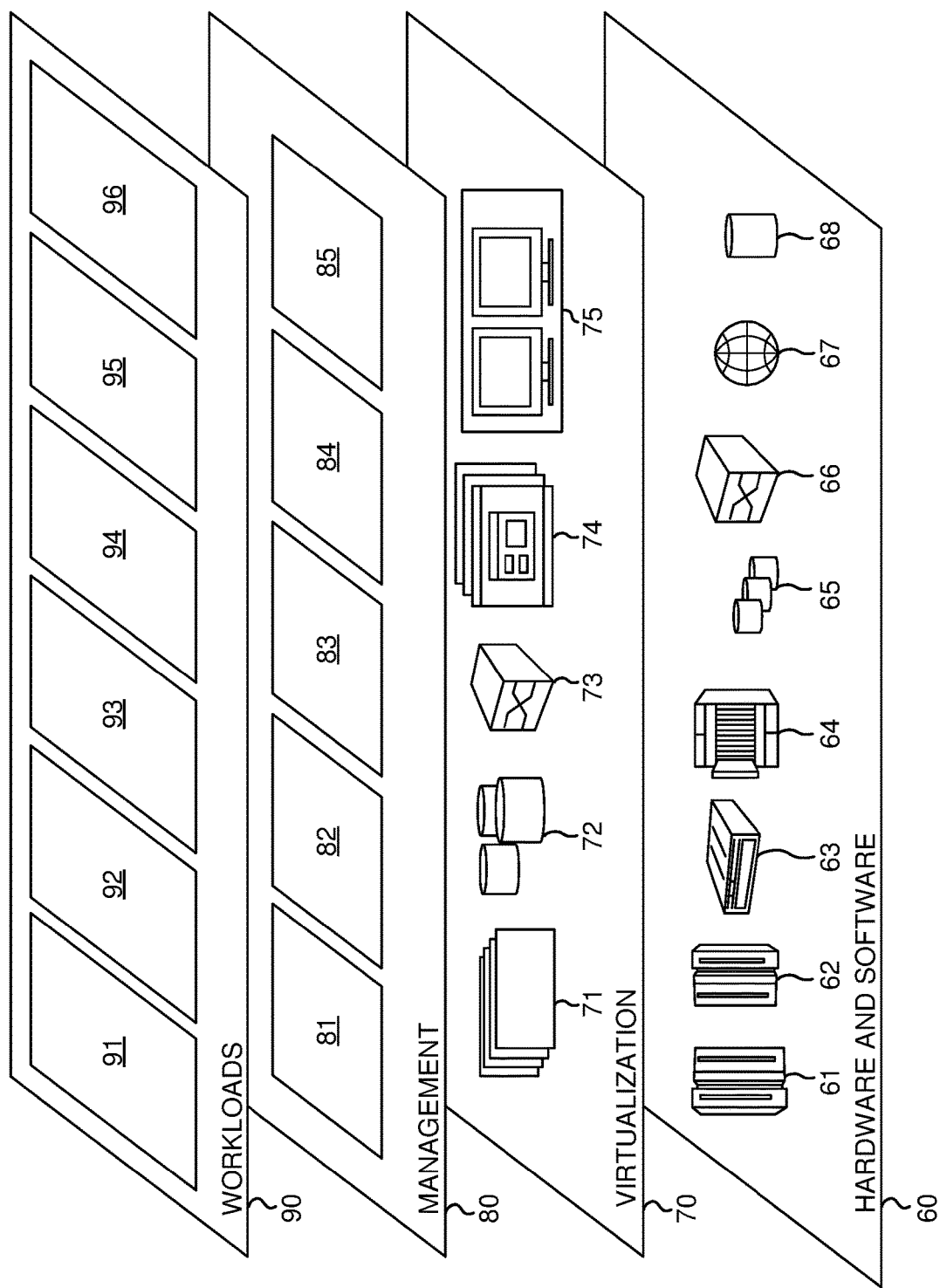
FIG. 7 is a block diagram illustrating abstraction model layers, in accordance with embodiments of the present disclosure.

Referring now to FIG. 7, a set of functional abstraction layers provided by cloud computing environment 50 (FIG. 6) is shown. It should be understood in advance that the components, layers, and functions shown in FIG. 7 are intended to be illustrative only and embodiments of the disclosure are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and medical management 96.

As discussed in more detail herein, it is contemplated that some or all of the operations of some of the embodiments of methods described herein can be performed in alternative orders or may not be performed at all; furthermore, multiple operations can occur at the same time or as an internal part of a larger process.

The present disclosure can be a system, a method, and/or a computer program product. The computer program product can include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure can be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions can execute entirely on the user's computer, partly on the user's computer, as a standalone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams can represent a module, segment, or portion of instructions, which comprises one or more executable instructions for implementing the specified logical function(s). In some alternative implementations, the functions noted in the block can occur out of the order noted in the figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the various embodiments. As used herein, the singular forms "a," "an," and "the" are intended to include the plural forms as well, unless the context clearly indicates otherwise. It will be further understood that the terms "includes" and/or "including," when used in this specification, specify the presence of the stated features, integers, steps, operations, elements, and/or components, but do not preclude the presence or addition of one or more other features, integers, steps, operations, elements, components, and/or groups thereof. In the previous detailed description of example embodiments of the various embodiments, reference was made to the accompanying drawings (where like numbers represent like elements), which form a part hereof, and in which is shown by way of illustration specific example embodiments in which the various embodiments can be practiced. These embodiments were described in sufficient detail to enable those skilled in the art to practice the embodiments, but other embodiments can be used, and logical, mechanical, electrical, and other changes can be made without departing from the scope of the various embodiments. In the previous description, numerous specific details were set forth to provide a thorough understanding the various embodiments. But the various embodiments can be practiced without these specific details. In other instances, well-known circuits, structures, and techniques have not been shown in detail in order not to obscure embodiments.

Different instances of the word "embodiment" as used within this specification do not necessarily refer to the same embodiment, but they can. Any data and data structures illustrated or described herein are examples only, and in other embodiments, different amounts of data, types of data, fields, numbers and types of fields, field names, numbers and types of rows, records, entries, or organizations of data can be used. In addition, any data can be combined with logic, so that a separate data structure may not be necessary. The previous detailed description is, therefore, not to be taken in a limiting sense.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Although the present disclosure has been described in terms of specific embodiments, it is anticipated that alterations and modification thereof will become apparent to the skilled in the art. Therefore, it is intended that the following claims be interpreted as covering all such alterations and modifications as fall within the true spirit and scope of the disclosure.

What is claimed is:

1. A method comprising:

receiving, by a processor, medical data associated with a user;

identifying, by the processor, a medical condition of the user based on the medical data wherein the medical condition is identified using a supervised machine learning algorithm built using training data of pre-classified images of the medical condition;

receiving object data of a plurality of objects in an environment of the user, wherein receiving object data includes receiving a set of object images in the environment of the user as captured on a camera of a device of the user;

analyzing the object data to determine an identity and characteristics of each object of the plurality of objects, wherein analyzing the object data further includes:

performing a region-based convolutional neural network (R-CNN) object detection on the set of object images, wherein an output of the R-CNN object detection includes an identity and a match certainty of each of the plurality of objects;

searching the identity of each of the plurality of objects output by the R-CNN object detection within an ontology to determine corresponding attributes of each of the plurality of objects;

comparing the plurality of objects to medical tools in a medical database using the characteristics within the object data;
identifying a subset of objects of the plurality of objects that match to respective medical tools within the medical database based on each object of the subset of objects sharing a threshold number of characteristics with each corresponding medical tool within the ontology;
identifying a medical procedure utilizing at least one object of the subset of objects to address the medical condition;
transmitting a recommendation that the medical procedure should be used to address the medical condition using the at least one object, wherein the recommendation is displayed as a formatted document for viewing, wherein the formatted document includes images of medical tools superimposing objects that match to respective medical tools, wherein the formatted document includes step-by-step instructions for carrying out the medical procedure, wherein instances of medical tools within the step-by-step instructions are replaced with corresponding matching objects;
receiving, from the user, a first feedback regarding the medical condition identified by the supervised machine learning algorithm;
updating the supervised machine learning algorithm based on the first feedback;
receiving, from the user, a second feedback regarding the identity and match certainty of each of the plurality of objects determined by the R-CNN object detection; and
updating the R-CNN object detection based on the second feedback.

2. The method of claim 1, wherein the medical condition is identified based on a number of matching characteristics between the medical condition and a known medical condition.

3. A system comprising:
a memory storing program instructions; and
a processor, wherein the processor is configured to execute the program instructions to perform a method comprising:
receiving, by the processor, medical data associated with a user;
identifying, by the processor, a medical condition of the user based on the medical data, wherein the medical condition is identified using a supervised machine learning algorithm built using training data of pre-classified images of the medical condition;
receiving object data of a plurality of objects in an environment of the user, wherein receiving object data includes receiving a set of object images in the environment of the user as captured on a camera of a device of the user;
analyzing the object data to determine an identity and characteristics of each object of the plurality of objects, wherein analyzing the object data further includes:
performing a region-based convolutional neural network (R-CNN) object detection on the set of object images, wherein an output of the R-CNN object detection includes an identity and a match certainty of each of the plurality of objects;
searching the identity of each of the plurality of objects output by the R-CNN object detection within an ontology to determine corresponding attributes of each of the plurality of objects;

comparing the plurality of objects to medical tools in a medical database using the characteristics within the object data;
identifying a subset of objects of the plurality of objects that match to respective medical tools within the medical database based on each object of the subset of objects sharing a threshold number of characteristics with each corresponding medical tool within the ontology;
identifying a medical procedure utilizing at least one object of the subset of objects to address the medical condition;
transmitting a recommendation that the medical procedure should be used to address the medical condition using the at least one object, wherein the recommendation is displayed as a formatted document for viewing, wherein the formatted document includes images of medical tools superimposing objects that match to respective medical tools, wherein the formatted document includes step-by-step instructions for carrying out the medical procedure, wherein instances of medical tools within the step-by-step instructions are replaced with corresponding matching objects;
receiving, from the user, a first feedback regarding the medical condition identified by the supervised machine learning algorithm;
updating the supervised machine learning algorithm based on the first feedback;
receiving, from the user, a second feedback regarding the identity and match certainty of each of the plurality of objects determined by the R-CNN object detection; and
updating the R-CNN object detection based on the second feedback.

4. The system of claim 3, wherein the medical procedure is identified by parsing keywords describing the medical condition within the medical database.

5. The system of claim 3, wherein a determination is made that the medical procedure requires at least one additional medical tool, wherein the method performed by the processor further comprises:
prompting the user to provide additional object data;
receiving the additional object data;
matching objects within the additional object data to medical tools within the medical database; and
determining, based on the matching, that the medical procedure can be completed using at least one object within the additional object data.

6. A computer program product comprising a computer readable storage medium having program instructions embodied therewith, the program instructions executable by a processor to cause the processor to perform a method comprising:
receiving, by the processor, medical data associated with a user;
identifying, by the processor, a medical condition of the user based on the medical data, wherein the medical condition is identified using a supervised machine learning algorithm built using training data of pre-classified images of the medical condition;
receiving object data of a plurality of objects in an environment of the user, wherein receiving object data includes receiving a set of object images in the environment of the user as captured on a camera of a device of the user;
analyzing the object data to determine an identity and characteristics of each object of the plurality of objects, wherein analyzing the object data further includes:

performing a region-based convolutional neural network (R-CNN) object detection on the set of object images, wherein an output of the R-CNN object detection includes an identity and a match certainty of each of the plurality of objects;

searching the identity of each of the plurality of objects output by the R-CNN object detection within an ontology to determine corresponding attributes of each of the plurality of objects;

comparing the plurality of objects to medical tools in a medical database using the characteristics within the object data;

identifying a subset of objects of the plurality of objects that match to respective medical tools within the medical database based on each object of the subset of objects sharing a threshold number of characteristics with each corresponding medical tool within the ontology;

identifying a medical procedure utilizing at least one object of the subset of objects to address the medical condition;

transmitting a recommendation that the medical procedure should be used to address the medical condition using the at least one object, wherein the recommendation is displayed as a formatted document for viewing, wherein the formatted document includes images of medical tools superimposing objects that match to respective medical tools, wherein the formatted document includes step-by-step instructions for carrying out the medical procedure, wherein instances of medical tools within the step-by-step instructions are replaced with corresponding matching objects;

receiving, from the user, a first feedback regarding the medical condition identified by the supervised machine learning algorithm;

updating the supervised machine learning algorithm based on the first feedback;

receiving, from the user, a second feedback regarding the identity and match certainty of each of the plurality of objects determined by the R-CNN object detection; and updating the R-CNN object detection based on the second feedback.

7. The computer program product claim 6, wherein the medical condition is identified based on a number of matching characteristics between the medical condition and a known medical condition.

8. The computer program product claim 6, wherein the medical procedure is identified by parsing keywords describing the medical condition within the medical database.

9. The computer program product claim 6, wherein a determination is made that the medical procedure requires at least one additional medical tool, wherein the method performed by the processor further comprises:

prompting the user to provide additional object data;
receiving the additional object data;
matching objects within the additional object data to medical tools within the medical database; and
determining, based on the matching, that the medical procedure can be completed using at least one object within the additional object data.

10. The computer program product of claim 6, wherein the program instructions are downloaded to the computer readable storage medium from a distributed data processing system.

* * * * *